United States Patent
Thomas et al.

(10) Patent No.: US 9,333,701 B2
(45) Date of Patent: May 10, 2016

(54) SYSTEMS AND METHODS FOR PROVIDING MICRO-ABERRATIONS ON FILM

(71) Applicant: Tredegar Film Products Corporation, Richmond, VA (US)

(72) Inventors: Paul Eugene Thomas, Terre Haute, IN (US); James Marion Myers, Clinton, IA (US)

(73) Assignee: TREDEGAR FILM PRODUCTS CORPORATION, Richmond, VA (US)

(*) Notice: Subject to any disclaimer, the term of this patent is extended or adjusted under 35 U.S.C. 154(b) by 0 days.

(21) Appl. No.: 14/097,448

(22) Filed: Dec. 5, 2013

(65) Prior Publication Data

US 2014/0151934 A1    Jun. 5, 2014

Related U.S. Application Data

(60) Provisional application No. 61/733,815, filed on Dec. 5, 2012.

(51) Int. Cl.
*B29C 59/06* (2006.01)
*B26F 1/26* (2006.01)
*B29C 59/04* (2006.01)
*A61F 13/511* (2006.01)
*A61F 13/15* (2006.01)

(52) U.S. Cl.
CPC .......... *B29C 59/06* (2013.01); *A61F 13/15731* (2013.01); *A61F 13/51104* (2013.01); *B26F 1/26* (2013.01); *B29C 59/04* (2013.01)

(58) Field of Classification Search
USPC .......................................................... 264/400
See application file for complete search history.

(56) References Cited

U.S. PATENT DOCUMENTS

| | | | |
|---|---|---|---|
| 4,797,246 A | 1/1989 | Reinke et al. | |
| 5,669,899 A * | 9/1997 | Osborn, III | 604/390 |
| 6,603,052 B2 * | 8/2003 | Davis et al. | 604/358 |
| 2002/0104609 A1 * | 8/2002 | Thomas | 156/178 |
| 2004/0123963 A1 * | 7/2004 | Chen et al. | 162/134 |
| 2004/0247833 A1 | 12/2004 | Copat et al. | |
| 2007/0031636 A1 | 2/2007 | Tribble et al. | |

* cited by examiner

*Primary Examiner* — Jacob Thomas Minskey
(74) *Attorney, Agent, or Firm* — Condo Roccia Koptiw LLP (57) ABSTRACT

Systems and methods for forming a vacuum formed, apertured film with micro-aberrations may be disclosed. For example, a polymer web such as a molten polymer web may be received at an engagement point between a screen with a positive aberration and a roller comprising a surface with a negative depression. The roller may have a diameter of no more than about 5.5 inches. A micro-aberration may be expanded, for example, on a land of the polymer web at the engagement point by inserting the positive aberration on the screen into the negative depression on the surface of the roller at a pressure of about 1.5 to about 3.5 pounds per linear inch (PLI). Additionally, one or more apertures are formed in the polymer web adjacent to a micro-aberration on a land.

16 Claims, 4 Drawing Sheets

SYSTEMS AND METHODS FOR PROVIDING MICRO-ABERRATIONS ON FILM

CROSS-REFERENCE TO RELATED APPLICATIONS

This application claims the benefit of U.S. Provisional Application No. 61/733,815, filed Dec. 5, 2012, which is hereby incorporated by reference herein.

BACKGROUND

An absorbent device is typically comprised of a topsheet, a fluid acquisition distribution layer, an absorbent core and a backsheet. The topsheet contacts the skin of the user of the device and transmits the fluid exudate toward the absorbent core which captures and stores it. The backsheet is the outermost layer and provides a liquid barrier against staining or soiling the clothing by preventing leakage or the passing of liquids stored in the core. Both the backsheet and the topsheet can be comprised of a thin layer of polymer film. "Thin" is historically in a general range of less than 50 microns but greater than 10 microns.

Since the advent of disposable diapers where a quiet material, absent from crinkling noise, was desired, it has been desired to impart a three dimensional aspect to any thin polymeric film used in absorptive devices. Such patterns of three dimensional protrusions and/or depressions typically provide the film layers with one or more following attributes: flexural softness and/or quietness due the 'pleating' aspect which lowers the resistance to the mechanical stress used to crumple or bend the film; lower gloss, or lack of sheen, by diffusing the reflected light; softness or silkiness to the touch, by creating a desired 'tactile' impression to the fingertips derived by pattern type and spacing and array, and specifically for tactile softness; a thinning which enables or allows a flexural bending as touch may be applied; an aesthetic appeal with patterns of flowers or ribbons or other designs found to be pleasing to a particular market segment of consumers; and the like. Additionally, one or more openings or apertures may be formed through the topsheet that may be vacuum formed to allow liquid to pass.

Unfortunately, current three-dimensional aspects that may be imparted or provided on the thin polymer films used for a topsheet may be limited in size (e.g. less than about 60 μm tall) when being vacuum formed due to the need to use high pressure to deform the web, and/or to avoid deflection and/or deformation of equipment used in vacuum forming, and/or to avoid disruption of the formation of the openings or apertures through the topsheet.

SUMMARY

Systems and methods for forming a vacuum formed, apertured film with micro-aberrations (e.g. that can be three-dimensional aspects) are provided. For example, in an embodiment, a polymer web such as a molten polymer web can be received at an engagement point between a screen with a positive aberration and a roller comprising a surface with a negative depression. The negative depression can be pre-formed in the surface of the roller. The roller can have a diameter of no more than about 5.5 inches and can be positioned at a leading edge of a vacuum slot.

According to an example embodiment, a micro-aberration can be expanded on the polymer web (e.g. on a land of the polymer web) at the engagement point by inserting the positive aberration on the screen into the negative depression on the surface of the roller with the film or polymer web therebetween. The positive aberration on the screen may be inserted into the negative depression on the surface of the roller (e.g. with the film or polymer web therebetween) at a pressure of about 1.5 to 3.5 pounds per lineal inch (PLI).

Additionally, one or more apertures can be formed through the molten polymer web by passing the molten polymer web with the micro-aberration beyond the leading edge of the vacuum slot such that the vacuum slot can pull portions of the polymer web into one or more openings included in the screen via a pressure differential. In an example embodiment, the micro-aberration can be formed on a land of the molten polymer web adjacent to the one or more apertures.

The Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to any limitations that solve any or all disadvantages noted in any part of this disclosure.

BRIEF DESCRIPTION OF THE DRAWINGS

A more detailed understanding of the embodiments disclosed herein may be had from the following description, given by way of example in conjunction with the accompanying drawings.

DETAILED DESCRIPTION

A detailed description of illustrative embodiments will now be described with reference to the various Figures. Although this description provides a detailed example of possible implementations, it should be noted that the details are intended to be exemplary and in no way limit the scope of the application.

Systems, methods, or processes are disclosed for expanding micro-aberrations on lands of a formed film topsheet such that a vacuum apertured formed film with micro-aberrations on the lands is produced. The micro-aberrations are a fine scale mesh with a high density per square area from approximately 5,500 to 55,000 per $cm^2$ and an average height of about 30 µm or greater, such as about 30 µm to about 200 µm, in an example embodiment and/or about 65 µm or greater, such as about 65 µm to about 200 µm, in another example embodiment. The micro-aberrations also include a tip or distal end that can be open or closed according to example embodiments.

To form such a micro-aberration, a positive aberration on one or more lands of an apertured formed film forming screen and a matching negative depression on an engaged roller is provided and used to expand or form a pattern of micro-aberrations.

It is known single-step processes can be used to form micro-aberrations on a film. Additional processes or process steps can then be used to subsequently form apertures in the film. For example, a film can be embossed with aberrations in one process or one step in a process. After such embossing, the film can be subsequently reheated in another process or in another step in a process to form the apertures (e.g. a pin can be used to perforate the reheated film with the micro-aberrations). Thus, currently, multiple processes or multiple-step processes can be used to form both micro-aberrations and apertures in polymeric films. Unfortunately, reheating the film to form the apertures tends to destroy the micro-aberrations formed in prior steps or processes.

For example, known processes using vacuum formation to make apertures in thin polymeric films include softening a thin polymer web in contact with a forming screen rotating over a vacuum slot as described, for example, in U.S. Pat. No. 4,151,240. Also known is a process where a molten web is introduced onto a forming screen rotating over a vacuum slot (e.g. as described in U.S. Pat. No. 4,456,570). Unfortunately, the structures formed from such processes do not reach a desired average height for the micro-aberrations (e.g. as shown in Table 2 below).

Examples of desired average heights for micro-aberrations in thin polymeric films with apertures are described, for example, in U.S. Pat. No. 4,629,643, where hydroforming or high pressure water stream imparting about 400-800 psig on a softened polymeric film is utilized to form micro-aberrations (see also, e.g., U.S. Pat. No. 7,521,588).

Also known for forming modifications to a polymeric film is the use of nip embossing as described, for example, in U.S. Pat. No. 3,950,480 and U.S. Pat. No. 5,229,186. A thin polymeric film that is softened is passed between two rolls, the nip being formed between the two rolls and the surface design on at least one of the rolls is embossed into the softened thin polymeric film. The nip embossed also relies on relatively high pressures to provide the modifications to the polymeric film.

Without being bound by a theory, it is believed that embossing thin polyolefin films with a fine mesh (e.g. density per square area from approximately 5,500 to 55,000 per cm$^2$) between two rollers uses a relatively higher pressure (PLI) within the range of 50 to 500 PLI like that utilized in, for example, U.S. Pat. No. 3,950,480 and U.S. Pat. No. 5,229,186, to deform the roller cover to the shape of the micro-aberrations to gain an average height of the micro-aberrations of a desired pattern in the resulting film.

It is also believed that this excess pressure used for embossing micro-aberrations, if applied in a vacuum apertured formed film process, would cause frictional drag across the fixed vacuum seal causing seal wear and early screen wear. The excessive pressure could also cause torsional stress that might bend and quickly break a thin, perforated, apertured formed film forming screen, as well as deflect the roller to where a uniform average height of micro-aberrations would not be possible. In standard embossing technology, it is typical to increase the roller diameter to as much as 3 to 6 feet in diameter to reduce the deflection that is caused by the high PLI requirements of embossing.

As described herein, a process such as vacuum forming process where a micro-aberration and an aperture can be formed without reheating (i.e. a single-step process) is provided. In such a process, micro-aberrations can be formed on the lands of an apertured formed film by introducing a molten polymer web between a positive aberration on an apertured formed film forming screen and a substantially aligned negative depression on a roller surface or cover and providing a low pounds per linear inch (PLI) pressure, such as about 1.5 to 4.0 PLI, from a roller that has a diameter of no more than 5.5 inches. Additionally, to form a film with micro-aberrations and apertures, the roller needs to be moved or integrated into the melt stream contact point of the process at the leading edge of the vacuum slot seal such that the roller does not block or disturb the air flow that is then used to form the apertures. To achieve this, the roller may not have a diameter greater than about 5.5 inches.

Figure 1:
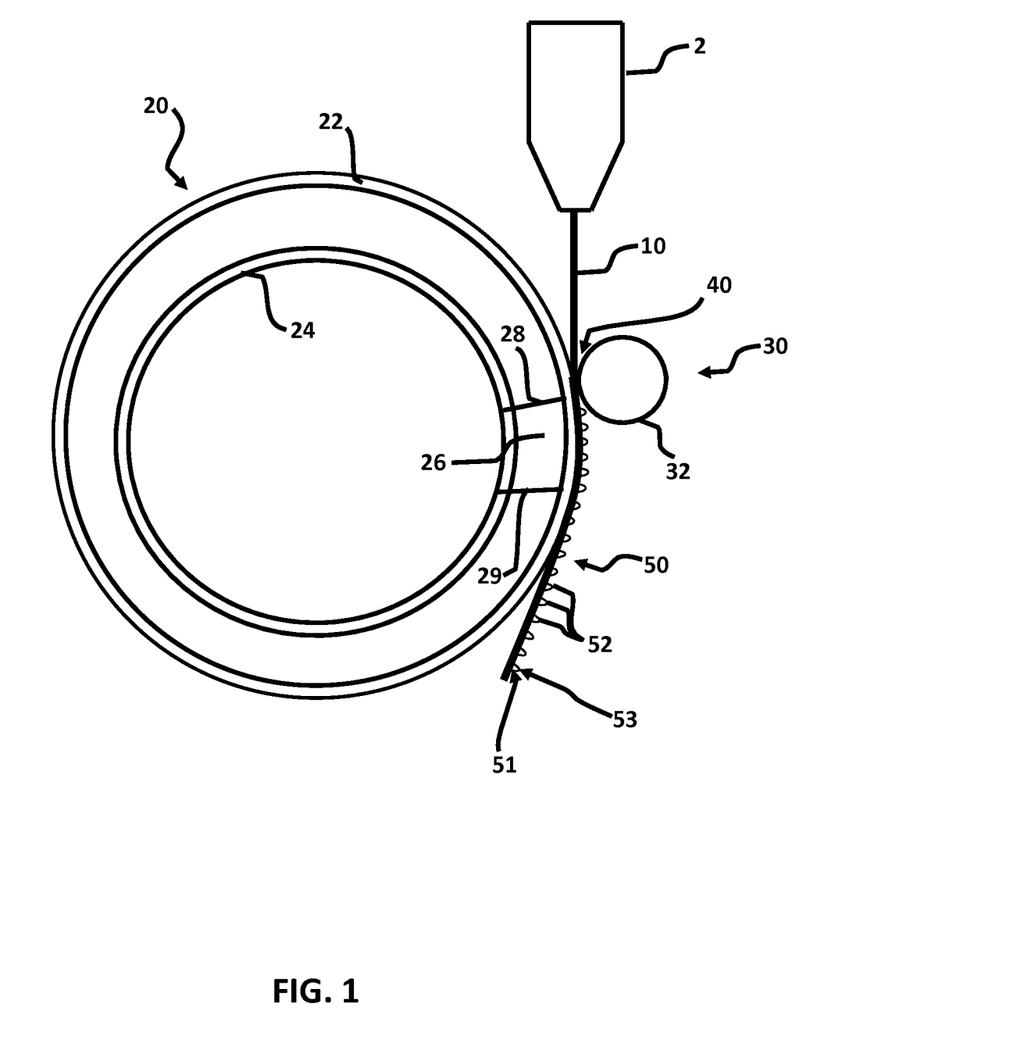
FIG. 1 depicts an example embodiment of a process or method for forming an apertured film with micro-aberrations.

FIG. 1 depicts an example embodiment of a process or method for forming an apertured film with micro-aberrations. As shown in FIG. 1, an extrusion slot die 2 introduces a molten polymer web 10 that is delivered to a forming screen assembly 20 and a roller assembly 30 at an engagement point 40.

The forming screen assembly 20 includes a screen 22 and a stationary manifold 24 around which the screen 22 rotates. The screen 22 includes one or more positive aberrations (not shown), for example, on one or more lands of the screen 22 that is used in combination with a matching negative depression (not shown), for example, in the roller 32 surface associated with the roller assembly 30 to expand micro-aberrations in the polymer web 10 such that a formed film topsheet (e.g. a vacuum apertured formed film) 50 with a pattern of one or more micro-aberrations 52 (not shown to scale) is made as described herein. Additionally, the screen 22 is perforated such that the screen 22 further includes openings (not shown) extending there-though that are adjacent to the lands with positive aberrations. The openings enable air to pass through the screen 22 such that screen 22, and the openings that are defined therethough, is used to form apertures in the polymer web 10.

As shown in FIG. 1, the stationary manifold 24, around which the screen 22 rotates, includes a stationary vacuum slot 26 with a leading edge 28 and a trailing edge 29. The vacuum slot 26 defined between the leading edge 28 and the trailing edge 29 includes a zone of a pressure differential, in the case of vacuum pressure, a negative pressure differential.

The roller assembly 30 includes a roller 32. As described herein, the roller 32 surface or cover includes one or more negative depressions (e.g. that are pre-pitted or pre-formed into roller 32). The one or more negative depressions are substantially aligned with the positive aberrations in the screen 22 (e.g. the one or more negative depressions mate with positive aberrations in the screen 22) at the engagement point 40 such that the roller 32 and the screen 22 is configured to cause the formation of a formed film topsheet 50 (e.g. a vacuum apertured formed film) with a pattern of one or more micro-aberrations 52 (not shown to scale).

After forming a micro-aberration at the engagement point 40, the polymer web 10 with a pattern of micro-aberrations formed thereon is then passed beyond the leading edge 28 and over the vacuum slot 26. The molten polymer web 10 suspended over the openings in the screen 22 is pulled into the openings in the screen 22 by the pressure differential created in the vacuum slot 26 such that apertures are formed in the regions of the polymer web 10 not supported by the lands of the screen 22. Convective cooling of the air passing through the newly formed apertures then removes sufficient heat from the molten web to cause it to change from the molten phase to the set phase, or crystalline phase for polyolefin polymers with crystalline structures such as polyethylene. When set, the polymer web 10 does not lose its newly formed shapes or structures for both the micro-aberrations and the apertures and/or the lands surrounding the apertures.

In one embodiment, as shown in FIG. 1, the roller 32 is positioned relative to the forming screen assembly 20 at the leading edge 28 such that the roller 32 is in virtually simultaneous contact with the polymer web 10 when delivered from the slot die 2 to the screen 22 at the engagement point 40.

The screen 22 rotates or moves such that the polymer web 10 with one or more apertures surrounded by lands and one or more micro-aberrations on the lands and passes beyond the trailing edge 29 of the vacuum slot 26. After passing over the trailing edge 29 of the vacuum slot 26, the polymer web 10 with the one or more micro-aberrations and one or more apertures surrounded by lands leaves the surface of the forming screen 22, such as being peeled off by a peel roller (not shown) and is now a vacuum apertured formed film topsheet 50 with a permanent pattern of one or more micro-aberrations 52 on the lands of the topsheet 50.

According to embodiments, the formed film topsheet 50 with the one or more apertures surrounded by lands and one or more micro-aberrations on the lands therethrough can further be provided to or passed to additional stations or equipment such that the formed film topsheet 50 is cut to desired width dimensions and wound in rolls for conversion as a component of any variety of absorptive devices and functions thereto.

Figure 2:
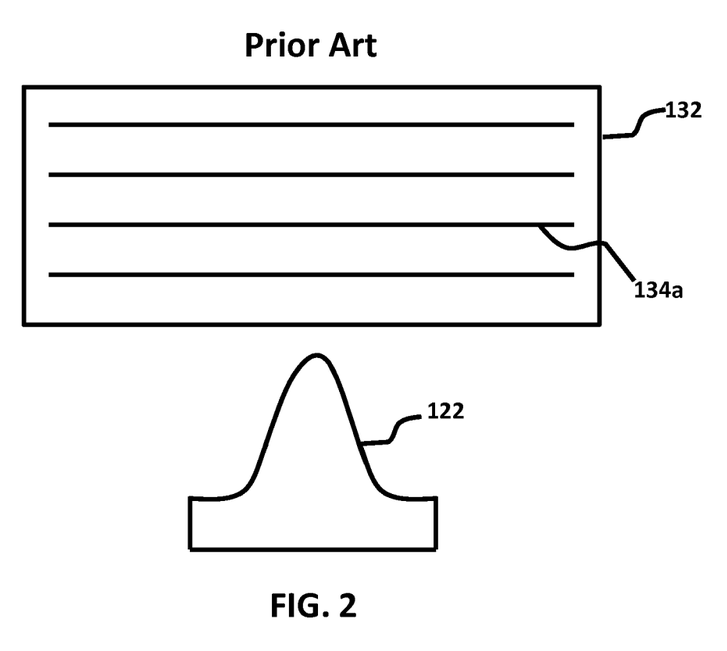
FIG. 2 depicts an example prior art surface or cover of a roller without a negative depression and a portion of an embossing roller with a positive aberration in a pre-engaged position.

FIG. 2 depicts an example of a portion of a prior art surface or cover of a large diameter nip roller without a negative depression (e.g. 132) and a portion of a roller such as a steel patterned roller with a positive aberration (e.g. 122) in a pre-engaged position (e.g. before being engaged at an engagement point such as the engagement point 40 described above in FIG. 1). The prior art surface or cover portion 132 is an example cover or surface currently available for an embossing roller. One typical cover would be comprised of a 65 Shore A Silicon Rubber, for example. For the sake of comparison herein, the roller of FIG. 2 comprising the surface or cover portion 132 could be located and orientated similarly to the roller 32 described above in FIG. 1 if it were possible to apply embossing methods to a vacuum apertured formed film process. Similarly, the aberration 122 on a portion of the steel embossing roller is an example representation of an aberration that is on a screen such as the screen 22 described above in FIG. 1. As shown in FIG. 2, the example prior art surface or cover portion 132 includes parallel horizontal striation lines 134a as a graphic representation of the unaltered, non-compressed state of the surface or cover portion 132 that also does not have a negative depression.

Figure 3:
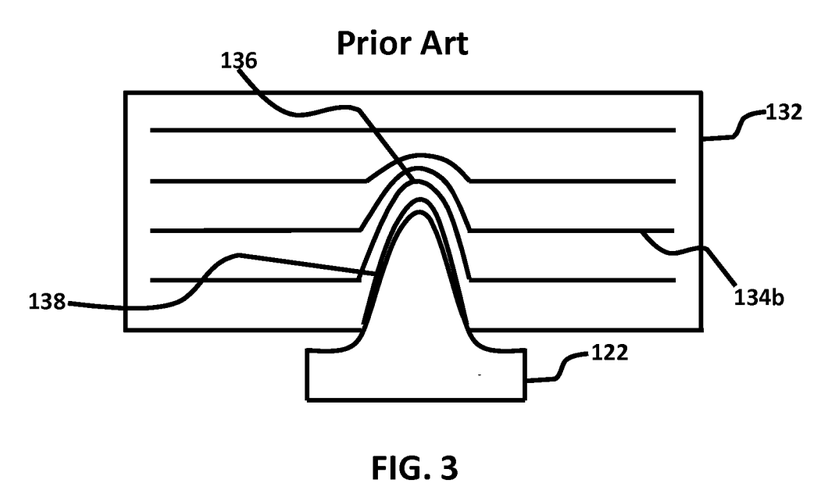
FIG. 3 depicts an example prior art surface or cover of a roller without a negative depression and a portion of an embossing roller with a positive aberration in an engaged position.

FIG. 3 depicts an example of a portion of a prior art surface or cover of a large diameter nip roller without a negative depression (e.g. 132) and a portion of a roller such as a steel patterned roller with a positive aberration (e.g. 122) in an engaged position. As shown in FIG. 3, striation lines 134b of the surface or cover portion 132 are altered (e.g. as shown by 136) when the positive aberration 122 is compressed or pressed into the surface of the surface or cover portion 132 at the engagement point when pressures from about 50 PLI up to 500 PLI are applied to cause the surface or cover portion 132 to comply with the shape of the aberration 122. When a thin layer of a polymer web (not shown) such as the polymer web 10 described in FIG. 1 is placed between the surface or cover portion 132 and the aberration 122, and high pressure from about 50 to 500 PLI is applied, a drag force that is associated with the compressed area 138 may cause a formation of a micro-aberration in the polymer web that corresponds to the shape of aberration 122. In this prior art embodiment, a low pressure (e.g. a PLI of about 1.5 to about 3.5, about 1.5 to about 4.0, and the like) would not provide sufficient pressure to force the surface of the surface or cover portion 132 to conform to the positive aberration 122 as described herein.

Additionally, in the prior art embodiment of FIG. 3, when the aberration 122 is then withdrawn from the surface or cover portion 132, a resiliency associated with the surface or cover portion 132 causes the surface or cover portion 132 to return to its pre-engaged shape shown in FIG. 2 where the striation lines 134b have returned to the original parallel position of striation lines 134a.

Figure 4:
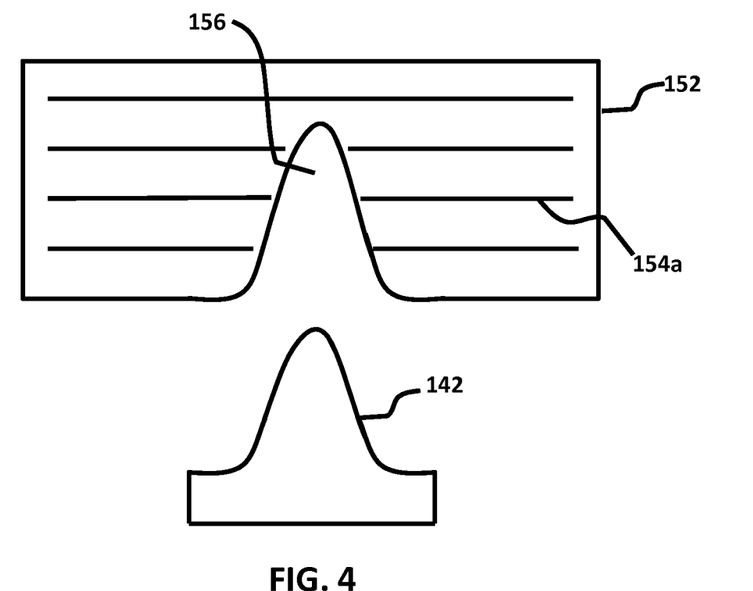
FIG. 4 depicts an example embodiment of a surface or cover of a roller with a negative depression and a portion of a screen with a positive aberration in a pre-engaged position that may be used to form an apertured film with micro-aberrations.

FIG. 4 depicts an example embodiment of a portion of a surface or cover portion of a roller (e.g. 152 with a negative depression (e.g. 156) and a portion of a screen having a positive aberration (e.g. 142) in a pre-engaged position. The surface or cover portion 152 of a roller represents the roller 32 described in FIG. 1 and an aberration 142 of a screen represents the screen 22 described in FIG. 1 in a pre-engaged position that is used in the present process to form a film with micro-aberrations. As shown in FIG. 4, the surface or cover portion 152 has a pre-formed cavity or negative depression 156. The cavity or negative depression 156 is pre-formed in a roller surface, for example, by laser engraving. Additionally, the cavity or negative depression 156 can have dimensions that closely or nearly match the shape of the aberration 142 except for the average depth of the cavity or negative depression 156, which is, for example, greater than an average height of the aberration 142 by at least about 15%. As shown in FIG. 4, graphic striation lines 154a represent the unaltered state while in the pre-engaged mode.

Figure 5:
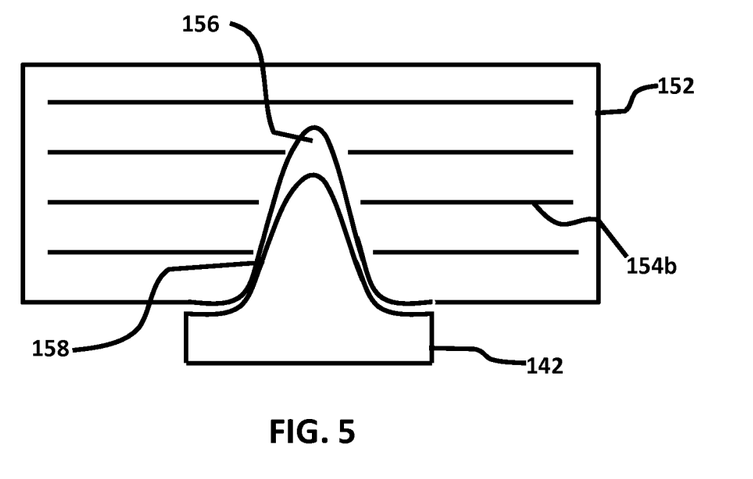
FIG. 5 depicts an example embodiment of a surface or cover of a roller with a negative depression and a portion of a screen with a positive aberration in an engaged position that may be used to form an apertured film with micro-aberrations.

FIG. 5 depicts an example embodiment of a portion of a surface or cover portion of a roller (e.g. 152) with a negative depression (e.g. 156) and a portion of a screen having a positive aberration (e.g. 142) in an engaged position. As shown in FIG. 5, the aberration 142 penetrates the cavity or negative depression 156. A polymer web such as the polymer web 10 in FIG. 1 is disposed between the surface or cover 152 and the aberration 142 of the screen (e.g. at an engagement point such as the engagement point 40). When pressure is applied, the aberration 142 penetrates the cavity or negative depression 156 to form a micro-aberration (e.g. an aberration with an average height of greater than 30 µm in an example embodiment or greater than about 65 µm in another example embodiment at a PLI of about 1.5 to 3.5. According to an embodiment, as shown in FIG. 5, a pinch point 158 may be created where the aberration 122 may penetrate and contact the cavity or negative aberration 156 prior to reaching a full depth of penetration. Additionally, as shown in FIGS. 4 and 5, graphic striation lines 154b remain virtually uncompressed and unaltered while in the engagement position.

Figure 6:
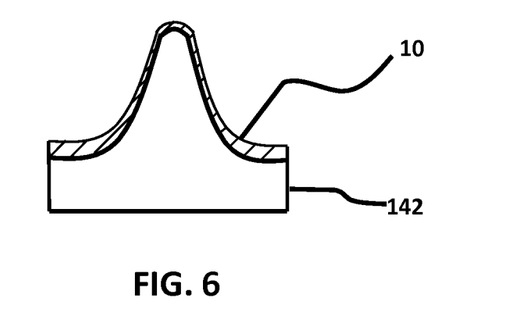
FIG. 6 depicts an example embodiment of a polymer web or film layer in proximity to a positive aberration that may be on a screen after an engagement point of the process or method of FIG. 1.

FIG. 6 depicts an embodiment of the polymer web 10 in proximity to an aberration (e.g. 142) beyond the engagement point 40 of the process or method described in FIG. 1. Accordingly, the polymer web 10, as shown, is still in proximity to aberration 142 after the micro-aberration is formed until being removed from the aberration and passed across the vacuum slot 26 as depicted in FIG. 1 to form apertures. The tip or distal end 20 of polymer web 10 may have become thinned or may have opened or both.

Roller

The roller 32 has particular dimensions such as a particular length, diameter, and the like to insure that the micro-aberrations are expanded substantially uniformly onto the surface of polymer web 10. For example, if the roller 32 has a diameter that is too large (e.g. 6 inches or more, for example), the roller 32 can block air flow into the vacuum slot 26 such that the apertures cannot properly form in the polymer web 10. Another negative effect of the roller 32 being too large in diameter is that it may attempt to form micro-aberrations on the polymer web 10 too early with too much time in the impingement area, releasing the melt too late such that one or more micro-aberrations may not form properly on the polymer web 10. As such, the roller 32 can have a diameter of about 2.0 inches to about 5.5 inches. In one embodiment, the roller 32 has a diameter of about 5.5 inches or less.

The roller 32 also provides sufficient pressure such as a pressure of about 1.5 to 3.5 PLI to expand micro-aberrations on the polymer web 10 and, as such, form a formed film topsheet 50 (e.g. a vacuum apertured formed film) with a pattern of micro-aberrations 52, but not too much pressure (e.g. greater than 3.5 PLI) such that the roller 32 may deform or deflect, thereby causing too great of a range of aberration height across the web where the low end of the height range are not functionally tall enough to provided desired benefits (e.g. greater 30 μm) at such a pressure (e.g. about 1.5 to 3.5 PLI) as shown in Table 2. Too little pressure (e.g. less than 1.5 PLI) does not sufficiently hold the roller 32 in the engagement position such that bouncing in and out of position may occur, which can damage the screen 22. Also, when bouncing 'out' the engagement is disengaged and no micro-aberrations are formed at that moment.

The roller 32 cover is most typically made of a coating with a Shore A hardness measurement of, for example, 20 to 95 and/or 65 to 90. In examples, the coating may be a rubber coating comprised of natural and synthetic rubbers such as natural rubber with a shore A hardness of 35-95, Ebonite® rubber with a Shore A hardness of 100, HNBR with a Shore A hardness of 30 to 95, Hypalon® rubber with a Shore A hardness of 40-95, Silicone rubber with a Shore A hardness of 35-75 and in an example a shore A hardness of 65, Neopree rubber with a Shore A hardness of 40-95, and the like. Other coatings may include plastic, acetal such as Delrin with a Shore A hardness of 80 to 95, and thermoset polymers. If one of these materials is chosen, the pre-formed negative depressions are typically laser engraved into the roller cover. Other options for covers for roller 32 may include layers of fabric with a Shore A hardness of 30 to 50, stiff foams with a Shore A hardness of 45 to 75, or felts with a Shore A hardness of 20 to 85. If the layers of fabric, stiff foams, or felts cover materials are selected, the pre-formed negative depressions are typically mechanically formed by constant repetition of pressure of a tool or other medium which has the same pattern array of the screen's 22 aberrations.

The pre-formed negative depressions described herein for fabric or stiff foam roller surfaces can be machined on a lathe or by running the roller 32 cover against the screen 22 for several repetitions and letting the screen 22 aberrations act as the machining tool. In such an embodiment, a matching alignment of negative depressions and aberrations are achieved. In embodiments, any other suitable material that may provide stability under pressure when forming one or more micro-aberrations 52 on the polymer web 10, as described herein, can be utilized for the roller 32 cover.

Polymer Web

The polymer web 10 is a molten polymer web that is maintained such that micro-aberrations are expanded from and in the polymer web 10. Vacuum apertured formed films (e.g. that can be used herein) can comprise polyolefin polymers, such as polyethylene and blends thereof, such as those described in Thomas U.S. Pat. No. 4,456,570. The polymer or polymer blend is in the molten phase or at a temperature above the temperature of melting (Tm) of the polymer or polymer blend used for the polymer web 10, such as a temperature of about 275° F. to 600° F. (135° C.-315° C.).

Screen

The screen 22 is, in an example, a metallic material such as nickel or may be any other suitable material (e.g. plastic, rubber or non-metallic materials) able to maintain its shape and strength under the described conditions of the process herein. As described above, in one embodiment, the screen 22 further has one or more openings of a certain shape and in a certain pattern, for example, surrounded by and adjacent to the positive aberrations on the lands of the screen 22.

Micro-Aberrations

The micro-aberrations 52 extend from a surface of the topsheet 50 and include proximal ends 51 (e.g. near the surface of the topsheet 50) and distal ends 53 (e.g. or a tip) opposite of the proximal ends 51. According to example embodiments, the micro-aberrations 52 can be opened at the proximal end 51, closed at the distal ends 53 (e.g. as shown in FIG. 1), opened at the distal ends 53 (not shown), opened and closed at the distal ends 53 (not shown), or any other suitable configuration. U.S. Pub. No. 2004/119207 at paragraph [0005] and paragraphs [0059]-[0063] discuses an example embodiment of open distal ends and closed distal ends. Additionally, U.S. Pat. No. 6,582,798 at Col. 7, lines 28-46 and Col. 9, lines 35-67 discusses an example embodiment of micro-aberrations 52 (e.g. called microridges).

Example

As stated previously, it is believed that the use of the roller surface prior art of FIG. 3, high PLI would need to be applied to form the desired micro-aberrations. For example, a PLI of over 125 would need to be applied to form the desired micro-aberrations of the embodiments disclosed herein (e.g. as shown in Table 2 below). In typical hardware configuration for embossing methods the rotating steel pattern roll rotates in a fixed position while the prior art large diameter nip roller such as that shown partially in FIG. 3 is pressed against a steel patterned roller by two air cylinders affixed to journals at the end of the prior art large diameter nip roller (e.g. as shown in U.S. Pat. No. 3,950,480). The PLI force at the contact point of the nip roller and steel patterned roller may be calculated by multiplying the air pressure (PSI) times the square area of an air cylinder's piston, times two air cylinders (total pounds force applied) divided by lineal inches of the width of the large diameter nip roller. The calculation of deflection value for a large diameter nip roller, due to the air cylinders pushing on each end of such a roller, is more complex, but common. Engineering calculations for deflection are available from rubber roll vendors who supply rubber nip rolls to the film and paper embossing industry.

If the roller 32 is 60 inches (152 cm) wide and has a total diameter of 4.0 inches (10.2 cm), which includes the 0.5 inch (1.27 cm) thickness of the resilient rubber cover, such deflections calculations can be made. For a calculation where the roller 32 further comprises a 0.50 inch (1.27 cm) of cover it also has a metal shaft of 3.0 inches (7.62 cm) in outside diameter (OD) with a wall thickness of 0.50 inch (1.27 cm) and, thus, an inside diameter (ID) of 2.0 inches (5.08 cm). The roller the has a total OD of 4.0 inches (10.2 cm) and is 60 inches (152 cm) long on the surface that will be engaged upon the screen.

For the data shown below in Table 1 the roller described above plus various PSI pressures where the input data for the deflection calculations.

TABLE 1

| Piston Diameter | PSI | PLI | Microns deflection of roller |
|---|---|---|---|
| 1.5 inch cylinder | 20 | 1.4 | 46 |
| 1.5 inch cylinder | 30 | 2.2 | 69 |
| 1.5 inch cylinder | 40 | 2.9 | 91 |
| 1.5 inch cylinder | 50 | 3.6 | 114 |
| 1.5 inch cylinder | 60 | 4.3 | 140 |
| 3.5 inch cylinder | 100 | 39.3 | 1257 |
| 3.5 inch cylinder | 120 | 47.1 | 1509 |
| 3.5 inch cylinder | 140 | 55.0 | 1758 |

For a system similar to that shown in FIG. 1 with a forming screen rotating over a fixed vacuum seal slot with a molten web extruding from a slot die, the data from Table 1 indicates that the formation of micro-aberrations of a desired average height of at least about 30 microns in an example embodiment or about 65 microns in another example embodiment will begin to lose formation uniformity due to roller deflection at PLI forces that are at or above about 3.5 (see also Table 2 below). Currently, at a PLI ranging over 3.5, even the micro-aberrations of average heights greater than 100 microns may not be formed uniformly across a 60 inch wide process due to impingement roller deflection. Most certainly at the standard 50 PLI and greater of the prior art for embossing aberration, the deflection for the small roller requirement of the vacuum apertured formed film process is astronomically prohibitive.

TABLE 2

FIG. 1 system with roller 32 material and surface structure

| | Max. PLI applied | Aberrations on Lands height, μm of the resulting film |
|---|---|---|
| Comparative Examples (FIGs. 2 and 3) | | |
| 1. Vacuum Only (no roller) | 0.0 | 19.9 |
| 2. 65 Shore A silicone Solid Rubber | 31.4 | 23.1 |
| | 62.8 | 30.3 |
| | 94.2 | 35.9 |
| | 125.7 | 37.9 |
| Example 1 | | |
| 65 Shore A Pitted Rubber FIGS. 1, 4, 5, 6 | 1.9 | 93.3 |
| | 2.4 | 102.8 |
| | 2.9 | 134.6 |
| | 3.3 | 148.2 |
| | 3.8 | 143.5 |

According to an embodiment, the comparative examples and examples in Table 2 were produced according to the process in FIG. 1 using a film, different rollers, and a forming screen that can include, for example, positive aberrations. In an example embodiment, the positive aberrations on the screen (e.g. the lands of the screen) used in Table 2 are virtually round arranged in an equilateral 60° triangular pattern spaced apart at 200 μm center-to-cent slightly tapering to an average height of 200 μm and an aspect ratio of 2.9 when their diameter at half their height is divided into their height value. Additionally, the film used in Table 2 can be a monolayer extruded and vacuum apertured film of 24.1 gsm (grams/square meter) basis weight (wt %) with a ratio of LDPE (0.922 gram/cm$^3$ density) to LLDPE (metallocene 0.918 g/cm$^3$ density) of about 2:1 and a TiO$_2$ (e.g. at about 3.8 wt %).

Although systems, methods, processes, and/or embodiments may be described herein with respect to various materials, techniques, equipment, such systems, methods, processes, and/or embodiments may be applicable to other applications and environments and may include additional materials, equipment and manufacturing techniques, methods, and/or processes in different orders than those disclosed herein.

What is claimed:

1. A method for forming a vacuum formed, apertured film with micro-aberrations, the method comprising:
    receiving a molten polymer web at an engagement point between a screen with a positive aberration and one or more openings adjacent to the positive aberration and a roller comprising a surface with a negative depression, wherein the roller is positioned at a leading edge of a vacuum slot;
    expanding a micro-aberration on a land of the molten polymer web at the engagement point by inserting the positive aberration on the screen into the negative depression on the surface of the roller with the molten polymer web therebetween at a pressure no more than about 3.5 pounds per lineal inch (PLI); and
    forming one or more apertures through the molten polymer web by passing the molten polymer web with the micro-aberration beyond the leading edge of the vacuum slot such that the vacuum slot is configured to pull portions of the polymer web into the one or more openings in the screen via a pressure differential.

2. The method of claim 1, wherein the negative depression is pre-formed in the surface of the roller.

3. The method of claim 2, wherein the negative depression is pre-formed in the surface of the roller by laser engraving a cover of the roller, wherein the cover of the roller comprises at least one of the following: rubber or thermoset polymer.

4. The method of claim 2, wherein the negative aberration is formed by repetitious mechanical pressure of a tool into a cover of the roller, wherein the cover of the roller comprises at least one of the following: fabric, stiff foam, or felts.

5. The method of claim 1, wherein the micro-aberration comprises a fine scale mesh of at least about 5,500 aberrations per square centimeter and an average aberration height of about 30 μm or greater.

6. The method of claim 1, wherein the roller comprises a diameter of no more than about 5.5 inches.

7. The method of claim 1, wherein the roller is engaged with the forming screen at no less than about 1.5 PLI.

8. The method of claim 1, wherein the micro-aberration is expanded on a land adjacent to the one or more apertures.

9. A method for forming a vacuum formed, apertured film with micro-aberrations, the method comprising:
    receiving a molten polymer web at an engagement point between a screen with a positive aberration and one or more openings adjacent to the positive aberration and a roller comprising a surface with a negative depression pre-formed therein, wherein the roller comprises a diameter of no more than about 5.5 inches, wherein the roller is positioned at a leading edge of a vacuum slot;
    expanding a micro-aberration on a land of the molten polymer web at the engagement point by inserting the positive aberration on the screen into the negative aberration on the surface of the roller with the molten polymer web therebetween, wherein the positive aberration on the screen is inserted into the negative depression on the surface of the roller at a pressure of about 1.5 to about 3.5 pounds per linear inch (PLI); and forming one or more apertures through the molten polymer web by passing the molten polymer web with the micro-aberration beyond the leading edge of the vacuum slot such that the vacuum slot is configured to pull portions of the polymer web into the one or more openings in the screen via a pressure differential.

10. The method of claim 9, wherein the micro-aberration comprises a fine scale mesh of at least about 5,500 aberrations per square centimeter with an average aberration height of about 30 μm or greater.

11. The method of claim 9, wherein the roller is engaged with the screen at no less than about 1.5 PLI.

12. The method of 9, wherein the surface of the roller further remains unaltered when the positive aberration is inserted into the negative depression pre-formed on the surface of the roller.

13. A method for forming a vacuum formed, apertured film with micro-aberrations, the method comprising:

receiving a molten polymer web at an engagement point between a screen with a positive aberration and one or more openings adjacent to the positive aberration and a roller comprising a surface with a negative depression therein, wherein the roller comprises a diameter of no more than about 5.5 inches, and wherein the roller is positioned at a leading edge of a vacuum slot;

expanding a micro-aberration on a land of the molten polymer web at the engagement point by inserting the positive aberration on the screen into the negative aberration on the surface of the roller with the molten polymer web therebetween, wherein the positive aberration on the screen is inserted into the negative depression on the surface of the roller at a pressure of about 1.5 to about 3.5 pounds per linear inch (PLI), and wherein the micro-aberration comprises a fine scale mesh of at least about 5,500 aberrations per square centimeter with an average aberration height of about 30 μm or greater; and forming one or more apertures through the molten polymer web by passing the molten polymer web with the micro-aberration beyond the leading edge of the vacuum slot such that the vacuum slot is configured to pull portions of the polymer web into the one or more openings in the screen via a pressure differential.

14. The method of claim 13, wherein the negative depression is pre-formed in the surface of the roller by laser engraving a cover of the roller, wherein the cover of the roller comprises at least one of the following: rubber or thermoset polymer.

15. The method of claim 13, wherein the negative aberration is formed by repetitious mechanical pressure of a tool into a cover of the roller, wherein the cover of the roller comprises at least one of the following: fabric, stiff foam, or felts.

16. The method of claim 13, wherein the roller is engaged with the screen at no less than about 1.5 PLI.

* * * * *